United States Patent [19]
Willert et al.

[11] Patent Number: 4,944,763
[45] Date of Patent: Jul. 31, 1990

[54] FIXING STEM FOR A PROSTHESIS

[75] Inventors: Hans-Georg Willert, Gottingen, Fed. Rep. of Germany; Rudolf Koch, Berlingen, Switzerland

[73] Assignee: Sulzer Brothers Limited, Winterthur, Switzerland

[21] Appl. No.: 393,525

[22] Filed: Aug. 11, 1989

[30] Foreign Application Priority Data

Aug. 24, 1988 [CH] Switzerland ............................ 3144/88

[51] Int. Cl.$^5$ .............................. A61F 2/36; A61F 2/30
[52] U.S. Cl. ............................................... 623/23; 623/16; 623/18
[58] Field of Search ........................ 623/16, 18, 20, 22, 623/23

[56] References Cited

U.S. PATENT DOCUMENTS 4,608,053  8/1986  Keller ..................................... 623/23

FOREIGN PATENT DOCUMENTS

| 0106945 | 5/1984 | European Pat. Off. | ............. 623/23 |
| 0169976 | 2/1986 | European Pat. Off. | ............. 623/23 |
| 0182176 | 5/1986 | European Pat. Off. | ............. 623/23 |
| 8236213 | 9/1985 | Fed. Rep. of Germany | ........ 623/23 |
| 2602672 | 2/1988 | France | ................................. 623/23 |
| 471394  | 5/1952 | Italy | ..................................... 623/23 |

Primary Examiner—Ronald L. Frinks
Attorney, Agent, or Firm—Kenyon & Kenyon

[57] ABSTRACT

The fixing stem is provided with a plurality of projections in the proximal region of the blade. Each projection is in the form of a pyramidal prism directed in a distal direction. The apex of each projection is sharp and is inclined at an acute angle to the surface of the blade. In addition, the projections are staggered along the length of the proximal region of the blade and are of decreasing height in the distal direction.

11 Claims, 1 Drawing Sheet

FIXING STEM FOR A PROSTHESIS

This invention relates to a fixing stem for a prosthesis. More particularly, this invention relates to a fixing stem for a hip joint prosthesis.

Heretofore, various types of fixing stems have been known for hip joint prosthesis. In some cases, the stems have been provided with various types of structures in order to improve on the fixation forces on the stem after implantation. For example, European patent application No. 0141022 describes a stem which has a plurality of projections in the form of continuous ribs which extend over the entire proximal zone of the stem. In addition, the ribs are formed on inclined angles such that the surfaces of the ribs are on a greater angle relative to the center plane of the stem than the troughs located between the ribs. The purpose of this arrangement is to provide for a displacement and compaction of the spongy tissue into which the stem is implanted. However, in practice, it has been found that the displacement and compaction of the spongy tissue which the ribs produce has not always been adequate. Further, these continuous ribs have, to some extent, a cutting effect when they penetrate into the relatively soft spongy tissue.

Other types of stems have also been provided with elongated ribs, such as described in French Patent No. 2,602,672, interrupted ribs, such as described in European patent application No. 0169976 and openings, such as described in European patent application No. 0182176. However, the displacement and compaction of the spongy tissue as well as the cutting effect remains in the cases where ribs are used whereas no compaction occurs where apertures are provided on a single rib or projecting shoulder.

Implants have also been provided with recesses along the length of a stem, such as described in European patent application No. 0106945 as well as with textured surfaces such as described in German Gebrauchsmuster No. 8236213.

Accordingly, it is an object of the invention to provide a fixing stem which provides greater displacement and compaction and less cutting action than previously known constructions.

It is another object of the invention to provide a fixing stem with an improved displacement and compaction arrangement in a proximal region for securement in spongy tissue.

Briefly, the invention provides a fixing stem for a prosthesis with a plurality of discrete projections in a proximal zone. In accordance with the invention, each projection is of pyramidal prism shape with an apex directed in a distal direction on an axis parallel to a longitudinal axis of the stem and inclined at an acute angle to the longitudinal axis.

The shape of the projections is such that the bases of the individual projections can be relatively wide to thus provide greater compaction of spongy tissue. If the base widths of the pyramidal prism shaped projections are made constant, the displacement or compaction of the spongy tissue into the "width" can be relatively constant, however, the manufacturing of constant base widths is relatively expensive.

The projections are also disposed in staggered relationship relative to each other in the direction of the longitudinal axis of the stem. In this respect, the axes of the respective projections do not align with each other during knocking-in of the stem into a bone so that a cutting effect is significantly reduced.

Advantageously, the projections at the proximal end of the zone have a greater base height than the projections at a distal end of the zone. Further, the ratio of the base height to length, i.e. a chord, of a projection is constant along the longitudinal axis of the stem. As a result, there is, to some extent, a homogeneous distribution of the angles for the resulting forces exerted by the flanks of the projection on the bone. These two features can reduce the explosive effect exerted by the entering implant peripherally on the bone. Conveniently, the edges of the projection projecting from the stem are sharp to facilitate entry into the spongy tissue.

These and other objects and advantages of the invention will become more apparent from the following detailed description taken in conjunction with the accompanying drawings wherein.

Figure 1:
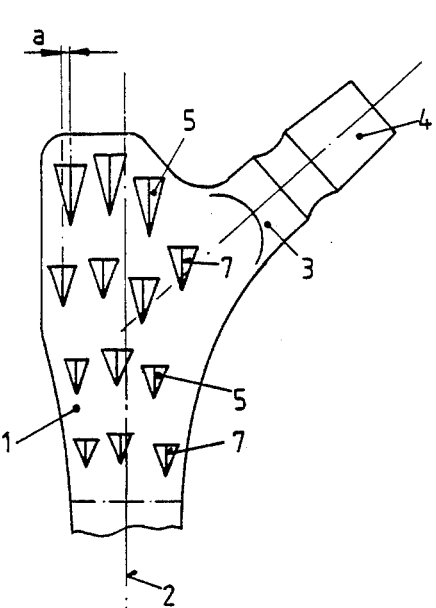
FIG. 1 illustrates a view in the ventral or dorsal direction of a proximal part of a fixing stem for a femur head prosthesis in accordance with the invention.

Referring to FIG. 1, the fixing stem 1 is constructed for use on a hip joint prosthesis.

Figure 2:
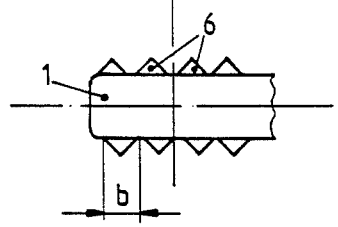
FIG. 2 illustrates a plan view of the stem of FIG. 1.

The fixing stem 1 includes a straight blade having a longitudinal axis as well as a rectangular cross-section as indicated in FIG. 2. In addition, a neck 3 extends upwardly from the blade and is attached to the blade without a collar. The neck 3 also carries a conical pin 4 which is adapted to receive a joint head (not shown) in a conventional manner.

The sides of the blade which extend in the anterior or posterior direction have pyramidal prism-shaped projections 5 which are distributed as a fixing structure over the proximal zone of the stem. As indicated in FIG. 1, each projection 5 has a cross sectional surface in the form of an equilateral triangle.

Figure 3:
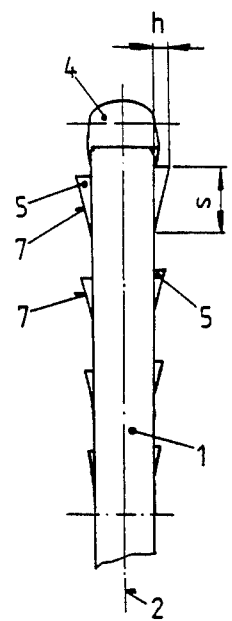
FIG. 3 illustrates a side view of the stem of FIG. 1.

Referring to FIG. 1, the widths b of the bases 6 of the projections 5 decrease in the direction from proximal to distal. As indicated in FIG. 1, each projection 5 has an apex 7 directed in the distal direction on an axis parallel to the longitudinal axis 2 of the stem while being inclined, as shown in FIG. 3, at an acute angle to the longitudinal axis 2. Each apex 7 is also shape.

As indicated in FIG. 3, the edge 7 of each projection 5 has a height h and a length measured along the surface of the stem 1, that is, along the chord wherein the ratio of the base height h to the length s is constant. As can be seen from FIG. 3, the base heights h of the projections 5 decrease from the proximal end of the zone toward the distal end with the overall effect that a wedging action boosting compaction of the spongy tissue is effective relative to the stem blade.

Further, as indicated in FIG. 1, the discrete projections 5 are staggered or offset relative to one another both along the longitudinal axis 2 of the stem and perpendicularly thereto. This serves to attenuate the cutting effect of the fixing structure. Advantageously, the offset or stagger a perpendicular to the longitudinal axis 2 is from 25% to 75% of the base width b.

The ratio of the base height h to the chord s of each projection 5 is constant. Thus, explosive forces exerted by the prosthesis and the fixing structure on a bone are reduced during implantation.

The invention thus provides a fixing stem with a fixing structure which provides for greater displacement and compaction in spongy tissue while lessening the cutting action of the fixing structure on the spongy tissue.

In addition, the invention provides a fixing structure for a stem of a prosthesis which reduces the explosive effect exerted by the implant upon entering a bone.

What is claimed is:

1. A fixing stem for a prosthesis having a plurality of discrete projections in a proximal zone, each said projection being of pyramidal prism shape having an apex directed in a distal direction and an axis directed in parallel to a longitudinal axis of the stem and inclined at an acute angle to said longitudinal axis, said projections having a constant ratio of base height to length along said longitudinal axis with said projections at a proximal end of said zone having a greater base height than projections at a distal end of said zone.

2. A fixing stem as set forth in claim 1 wherein said projections have a constant base width.

3. A fixing stem as set forth in claim 1 wherein said projections are disposed in staggered relationship relative to each other in the direction of said longitudinal axis.

4. A fixing stem as set forth in claim 1 wherein said axis of each projection is offset perpendicularly of said longitudinal axis from an axis of a projection spaced longitudinally therefrom an amount of from 25% to 75% of a base width thereof.

5. A fixing stem as set forth in claim 1 wherein each apex is sharp.

6. A fixing stem for a hip joint prosthesis comprising
a straight blade having a longitudinal axis;
a neck extending from said blade; and
a plurality of projections extending from opposite sides of said blade in a proximal zone thereof, each projection being of pyramidal prism shape with an apex directed in a distal direction on an axis parallel to said blade axis and on an inclined angle to said blade axis, said projections having a constant ratio of base height to length along said longitudinal axis with said projections at a proximal end of said zone having a greater base height than projections at a distal end of said zone.

7. A fixing stem as set forth in claim 6 wherein said projections are disposed in staggered relationship relative to each other in the direction of said longitudinal axis.

8. A fixing stem as set forth in claim 7 wherein said axis of each projection is offset perpendicularly of said longitudinal axis from an axis of a projection spaced longitudinally therefrom an amount of from 25% to 75% of a base width thereof.

9. A fixing stem for a hip joint prosthesis comprising
a straight blade having a longitudinal axis;
a neck extending laterally from said blade;
a pin extending from said neck; and
a plurality of projections extending from opposite anterior and posterior sides of said blade in a proximal zone thereof, said projections being disposed in staggered relationship relative to each other in the direction of said longitudinal axis, each projection being of pyramidal prism shape with an apex directed in a distal direction on an axis parallel to said longitudinal blade axis and on an inclined angle to said blade axis.

10. A fixing stem as set forth in claim 9 wherein said axis of each projection is offset perpendicularly of said longitudinal axis from an axis of a projection spaced longitudinally therefrom an amount of from 25% to 75% of a base width thereof.

11. A fixing stem as set forth in claim 9 wherein said projections have a constant ratio of base height to length along said longitudinal axis and said projections at a proximal end of said zone have a greater base height than projections at a distal end of said zone.

* * * * *